US00PP24360P3

(12) United States Plant Patent
Rabideau

(10) Patent No.: US PP24,360 P3
(45) Date of Patent: Apr. 1, 2014

(54) ***PIERIS JAPONICA* PLANT NAMED 'CONRABIDEAU'**

(50) Latin Name: *Pieris japonica*
Varietal Denomination: Conrabideau

(75) Inventor: Ronald R. Rabideau, Jackson, NJ (US)

(73) Assignee: CP Delaware, Inc., Wilmington, DE (US)

( * ) Notice: Subject to any disclaimer, the term of this patent is extended or adjusted under 35 U.S.C. 154(b) by 81 days.

(21) Appl. No.: 13/506,573

(22) Filed: Apr. 30, 2012

(65) Prior Publication Data

US 2013/0291239 P1 Oct. 31, 2013

(51) Int. Cl.
*A01H 5/00* (2006.01)

(52) U.S. Cl.
USPC ..... Plt./226

(58) Field of Classification Search
USPC ..... Plt./226
See application file for complete search history.

*Primary Examiner* — Susan McCormick Ewoldt
(74) *Attorney, Agent, or Firm* — Buchanan Ingersoll & Rooney PC

(57) ABSTRACT

A new and distinct *Pieris japonica* plant is provided that was discovered as a spontaneous mutation of unknown causation of the 'Valley Valentine' variety (non-patented in the United States). The new plant was discovered during April 2000 when present in a controlled environment among a population of 'Valley Valentine' plants that had been asexually reproduced by tissue culture. The new plant displays an attractive upright well-branched generally uniform moderately vigorous growth habit. Large clusters of pink flowers are displayed. The attractive new growth displays a brick red coloration. The foliage is variegated green with irregularly presented yellow margins when mature. The plant is well suited for providing attractive ornamentation throughout the year.

2 Drawing Sheets

Botanical/commercial classification: *Pieris japonica*/ Japanese Andromeda Plant.

Varietal denomination: cv. Conrabideau.

SUMMARY OF THE INVENTION

*Pieris japonica*, commonly known as Japanese Andromeda, is recognized to be widely grown broad-leaved evergreen plant that is grown to provide ornamentation.

The new *Pieris japonica* plant was discovered during April 2000 at Jackson, N.J., U.S.A., among a population of *Pieris japonica* plants of the 'Valley Valentine' variety (non-patented in the United States) that were being grown in a nursery setting. The population of plants resulted from the asexual propagation of the 'Valley Valentine' variety by the use of tissue culture. The new variety of the present invention is believed to be a spontaneous mutation of unknown causation. A single plant of the new variety was found to have a distinctive combination of characteristics, was carefully preserved, and thereafter has been evaluated in detail over an extended period of time. Had the new variety of the present invention not been discovered and preserved it would have been lost to mankind.

It has been confirmed that the characteristics of the new plant are reliably expressed.

It has been found that the new plant of the present invention displays the following combination of characteristics:

(a) displays an attractive upright well-branched generally uniform moderately vigorous growth habit,
(b) forms large clusters of pink flowers,
(c) forms attractive new growth having a brick red coloration,
(d) forms attractive variegated green foliage with irregularly presented yellow margins when mature, and
(e) is well suited for providing distinctive ornamentation.

The new plant of the present invention can be grown to advantage to provide attractive ornamentation in areas where a relatively low-growing evergreen plant is desired. It can be used as a slow-growing foundation planting and/or as a specimen planting. Attractive colorful ornamentation is made possible throughout the year.

The new variety of the present invention can be distinguished from its mother plant of the 'Valley Valentine' variety, and all other *Pieris japonica* varieties known to the discoverer.

For instance, the new variety can be distinguished from the popular 'Valley Valentine' variety in view of the formation of variegated leaves unlike the 'Valley Valentine' variety.

The new variety also can be distinguished from other *Pieris japonica* varieties that display variegated leaves, such as the 'Flaming Silver' variety (non-patented in the United States), the 'FIRE N ICE' variety (U.S. Plant Pat. No. 19,994), and the 'Ralto' variety (U.S. Plant Pat. No. 19,331). The 'Flaming Silver' and 'FIRE N ICE' varieties each display white flowers unlike the pink flowers of the new variety of the present invention. The 'Ralto' variety has been found to display a lesser number of lowers per inflorescence, an overall inflorescence of having a lesser diameter, and a flower display having a shorter lastingness on the plant. More specifically, the new variety commonly displays (a) approximately 325 flowers per inflorescence vs. approximately 200 flowers per inflorescence for the 'Ralto' variety, (b) a wider inflorescence presentation of approximately 12.5 cm on average vs. approximately 10.6 cm on average for the 'Ralto' variety, and (c) a longer flower lastingness on the plant of approximately three weeks vs. approximately two weeks for the 'Ralto' variety. The foliage of the new variety has been found to be substantially similar to that of the later discovered 'Ralto' variety.

The characteristics of the new variety have been confirmed at West Grove, Pa., U.S.A., to be strictly transmissible by asexual propagation through the rooting of cuttings from one generation to another. When propagated during mid-July at West Grove, Pa., U.S.A., by the use of cuttings, good root initiation has been observed within approximately eight weeks.

The new variety has been named 'Conrabideau', and will be marketed under the ANGEL FALLS trademark.

BRIEF DESCRIPTION OF THE PHOTOGRAPHS

The accompanying photographs show, as nearly true as it is possible to make the same in color illustrations of this character, a typical plant and plant parts of the new variety. The illustrated plants were approximately four years of age and were observed while growing in containers at West Grove, Pa., U.S.A. Such plants had been asexually reproduced by the rooting of cuttings.

DETAILED BOTANICAL DESCRIPTION

Figure 1:
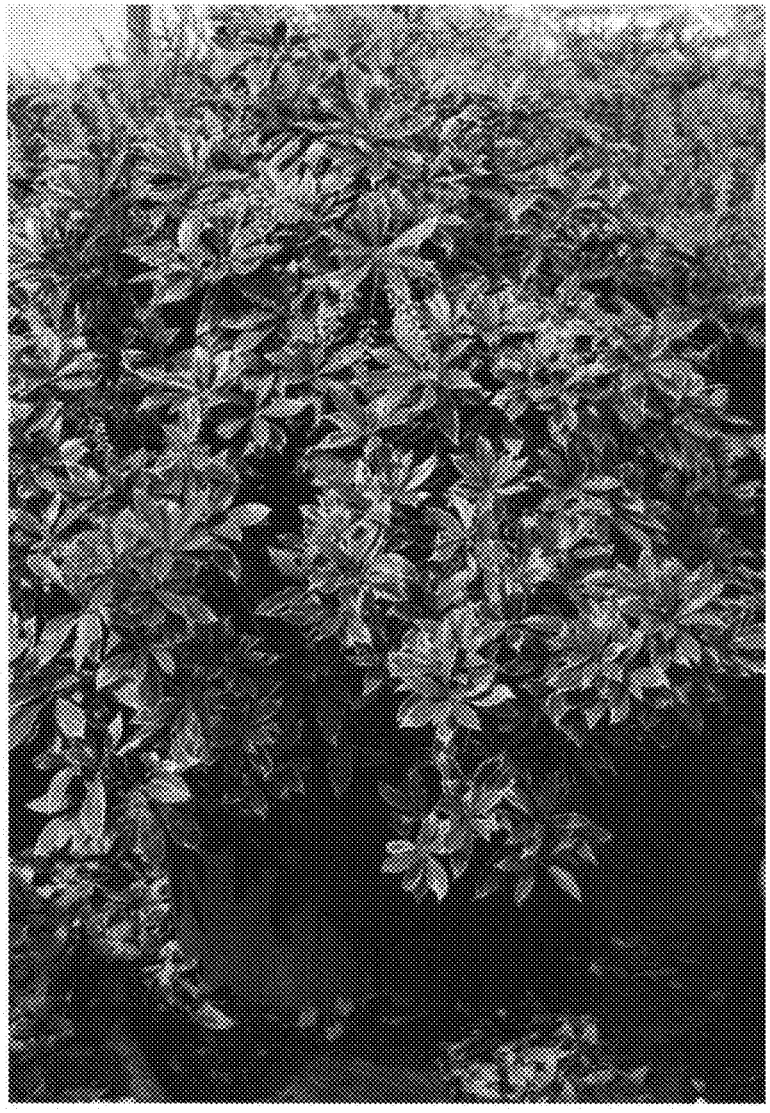
FIG. 1 illustrates the overall compact and well-branched and generally uniform growth habit of the new variety in the spring prior to full blossoming.
Figure 2:
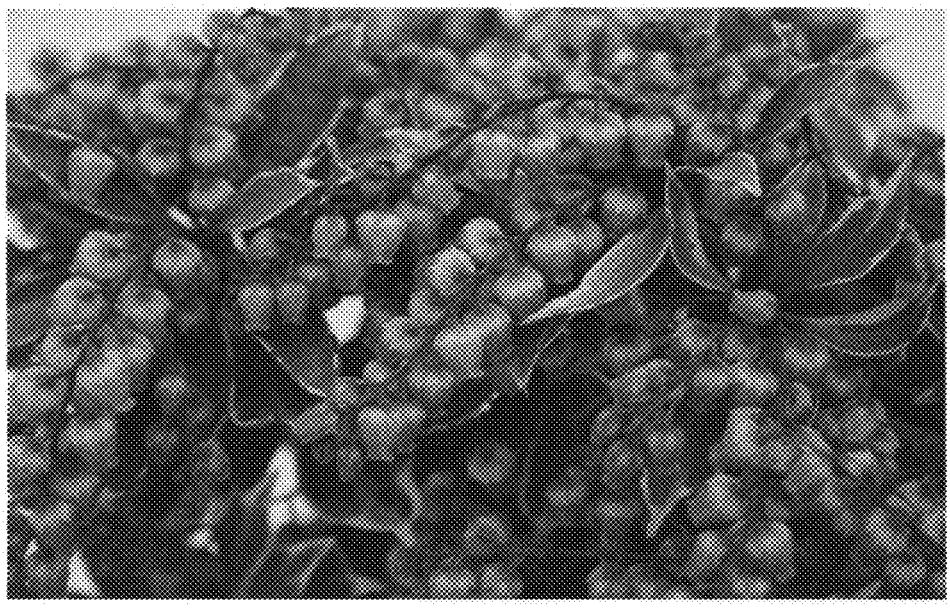
FIG. 2 illustrates a closer view of the attractive pink flower clusters when mature together with the variegated green leaves which display irregularly variegated yellow margins.

The chart used in the identification of colors is that of The Royal Horticultural Society (R.H.S. Colour Chart), London, England (1995 Edition, or equivalent). The description is based on the observation of five-year-old specimens of the new variety during May while growing in containers under artificial light in a greenhouse at West Grove, Pa., U.S.A.

Botanical classification: *Pieris japonica*, cv. 'Conrabideau'.

Type: Shrub evergreen.

Plant:

*Growth habit*.—Upright, and moderately vigorous.

*Height*.—Approximately 5 feet on average for a five-year-old plant.

*Width*.—Approximately 3 feet on average for a five-year-old plant.

*Branching*.—Well-branched to form a generally uniform plant.

*Trunk diameter*.—Commonly approximately 2.5 inches measured one inch above the soil.

*Trunk texture*.—Rough.

Branches:

*When young*.—When approximately one year of age approximately 5 mm in diameter, and near Yellow-Green Group 144B in coloration.

*When mature*.—Near the base of the plant approximately 1 cm in diameter, and near Grey-Brown Group 199A in coloration.

*Branch color*.—Commonly near Greyed-Orange Group 174A.

Foliage:

*Leaf type*.—Simple.

*Leaf arrangement*.—Alternate-leaved.

*Leaf shape*.—Generally elliptical.

*Leaf apex*.—Acuminate.

*Leaf base*.—Attenuate.

*Leaf texture*.—Smooth.

*Venation*.—Cross-venulate, and near Yellow-Green Group 145A in coloration.

*Juvenile foliage*.—Color upper surface: when fully unfolded and the leaf shape is apparent, some leaves are Greyed-Red Group 179A in coloration with tips of White Group 155A, and some leaves are Green Group 143B with margins near Greyed-Red Group 179C. Color under surface: when fully unfolded and the leaf shape is apparent, the leaf coloration commonly is Greyed-Red Group 179C to Green Group 142C with tones of Greyed-Red Group 179C.

*Semi-mature foliage*.—Color upper surface. near Yellow-Green Group 145A with irregularly configured leaf margins of near White Group 155A. Color under surface: near Yellow-Green Group 145B with darker venation of near Yellow-Green Group 145A and irregularly configured coloration at leaf margins of near White Group 155A.

*Fully mature*.—Color upper surface: near Green Group 137A with irregularly configured coloration at leaf margins of near Yellow Group 2D. Color under surface: near Green Group 138B with darker venation of near Green Group 137A and irregularly configured coloration at leaf margins of near Yellow Group 2D.

*Petioles*.—Length: approximately 1.3 cm on average. Diameter: approximately 2 mm on average. Color: near Yellow-Green Group 145A.

Inflorescence:

*Season*.—April to May at West Grove, Pa., U.S.A.

*Arrangement*.—Commonly in clusters of approximately 325 flowers on terminal paniculate racemes which initially are substantially upright and subsequently with maturity tend to bend to a weeping disposition.

*Length*.—Commonly approximately 7 cm.

*Width*.—Commonly approximately 12.5 cm.

*Buds*.—Length: approximately 6 mm. Width: approximately 4 mm. Shape: generally oval. Color: near Red-Purple Group 58A, commonly with White Group 155A towards the base.

*Flowers*.—Type: bell-shaped, urceolate with a single whorl of five petals, and persistent. Petals: fused at the base. Length: commonly approximately 6 mm. Width: commonly approximately 5 mm. Petal shape: generally ovate with an obtuse apex. Petal margin: entire. Petal texture: glabrous on upper and under surfaces. Petal color when opening: on the outer surface near Red-Purple Group 59A and White Group 155A towards the base, and on the inner surface near Red-Purple Group 70C blended with White Group 155A. Petal color when fully open: on the outer surface near Red-Purple Group 60B and White Group 155A towards the base, and on the inner surface near Red-Purple Group 70C blended with White Group 155A. Petal color after about three weeks: commonly lightens to near Red-Purple Group 70D. Fragrance: very light, sweet and pleasant. Flower longevity: approximately three weeks on the plant. Stamen number: approximately 10 per flower. Anther shape: oval. Anther length: approximately 2 mm. Anther color: near Brown Group 200A. Pollen formation: sparse. Pollen color: near Greyed-Orange Group 167C. Pistil number: one per flower. Style length: approximately 4 mm. Style color: near White Group 155A. Stigma shape: narrowly oval. Stigma diameter: approximately 0.5 mm. Stigma color: near Yellow-Green Group 145B. Ovary color: near Yellow-Green Group 144A overlaid with Yellow-Green Group 144C. Seeds and fruit: none observed during observations to date.

*Sepals*.—Arrangement: five, fused in a single whorl. Length: approximately 3 mm. Width: approximately 1 mm at the widest point. Shape: somewhat ovate. Apex: acute. Base: broadly cuneate. Texture: glabrous on upper and lower surfaces. Immature color: near Greyed-Purple Group 187B. Mature color: near Red-Purple Group 60B blending with White Group 155A at the apex.

*Peduncles*.—Length: commonly approximately 1.2 cm on average. Diameter: commonly approximately 2 mm on average. Color: near Greyed-Purple Group 187B in coloration.

*Pedicels*.—Length: commonly approximately 4 mm. Diameter: commonly approximately 0.5 mm. Disposition: commonly approximately 40 degrees from the vertical. Strength: moderately strong. Texture: glabrous. Color: near Greyed-Purple Group 183B.

Development:

*Tolerance to diseases*.—Believed to be typical of the species.

*Resistance to pests*.—Believed to be typical of the species.

*Tolerance to heat*.—Has withstood a temperature of 100° F. in absence of sun burning at West Grove, Pa., U.S.A.

*Tolerance to cold*.—Has withstood a temperature of 0° F. in the absence of winter burning at West Grove, Pa., U.S.A.

The new 'Conrabideau' variety has not been observed to date under all possible environmental conditions. Accordingly, it is possible that the phenotype may vary somewhat with variations in the environment, such as temperature, light intensity, day length, and other cultural conditions without variance of the genotype.

I claim:

1. A new and distinct *Pieris japonica* plant characterized by the following combination of characteristics:

(a) displays an attractive upright well-branched generally uniform moderately vigorous growth habit, (b) forms large clusters of pink flowers, (c) forms attractive new growth having a brick red coloration, (d) forms attractive variegated green foliage with irregularly presented yellow margins when mature, and (e) is well suited for providing distinctive ornamentation; substantially as shown and described.

* * * * *